United States Patent [19]

Tamura et al.

[11] Patent Number: 4,740,586
[45] Date of Patent: Apr. 26, 1988

[54] CRYSTALLINE FORM III OF N$^\alpha$-[[(S)-4-OXO-2-AZETIDINYL]-CARBONYL]-L-HISTIDYL-L-PROLINAMIDE

[75] Inventors: Toshinari Tamura; Hideya Matsuda; Makoto Yoshida, all of Saitama, Japan

[73] Assignee: Yamanouchi Pharmaceutical Co., Ltd., Tokyo, Japan

[21] Appl. No.: 937,608

[22] Filed: Dec. 3, 1986

[30] Foreign Application Priority Data

Dec. 6, 1985 [JP] Japan .................................. 60-275686

[51] Int. Cl.$^4$ ........................................... C07D 205/08
[52] U.S. Cl. ..................................... 530/331; 540/200
[58] Field of Search ......................... 530/331; 540/200

[56] References Cited

U.S. PATENT DOCUMENTS 4,537,900  8/1985  Kreidl et al. .................... 548/342 X
4,564,609  1/1986  Tamura et al. ....................... 514/18

OTHER PUBLICATIONS

Haleblian, J. et al., *J. Pharm. Sci.*, 58(8), 913–917 (1969).

*Primary Examiner*—Richard A. Schwartz
*Attorney, Agent, or Firm*—Burgess, Ryan & Wayne

[57] ABSTRACT

A novel crystal form of N$^\alpha$-[[(S)-4-oxo-2-azetidinyl]-carbonyl]-L-histidyl-L-prolinamide is provided and a process for preparing such crystals. The crystals provided by the present invention are the dihydrate form of the compound which exhibits a specific X-ray powder diffraction pattern, infared absorption spectrum and thermogravimetry-differential scanning calorimetry. The compound in its novel crystal form is useful in the treatment of consciousness disturbances and memory disorders.

1 Claim, 12 Drawing Sheets

FIG. I

CRYSTALLINE FORM III OF N$^\alpha$-[[(S)-4-OXO-2-AZETIDINYL]-CARBONYL]-L-HISTIDYL-L-PROLINAMIDE

FIELD OF THE INVENTION

This invention relates to novel crystals of N$^\alpha$-[[(S)-4-oxo-2-azetidinyl]carbonyl]-L-histidyl-L-prolinamide (hereinafter, is referred to as Compound A) shown by the formula

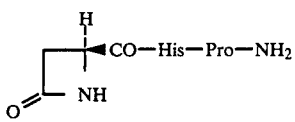

and a process for producing the crystals. More particularly, the invention relates to the Form III crystals of Compound A and a process for producing them.

BACKGROUND OF THE INVENTION

Compound A is a known compound described in Japanese patent publication (Unexamined) Nos. 225,182/84, 172,996/85, and U.S. Pat. No. 4,564,609 as a compound having improving activities for consciousness disturbance and memory disorder.

Each example 1 of the aforesaid patent publications describes that Compound A was crystallized by triturating with a small amount of methanol and the resulting crystals contained ½ mol of water on the basis of the elemental analysis.

SUMMARY OF THE INVENTION

As the result of various investigations, the inventors have succeeded in obtaining novel crystals of Compound A, which are different from the above crystals in the water content, by a new crystallization method.

The crystals of Compound A thus obtained are 4 kinds of Forms II, III, IV and V. Form II is a monohydrate, Form III, the crystals of this invention, is a dihydrate, and Forms IV and V are anhydrides.

DETAILED DESCRIPTION OF THE INVENTION

The physicochemical properties of these crystals of Compound A thus obtained are shown below.

Figure 1:
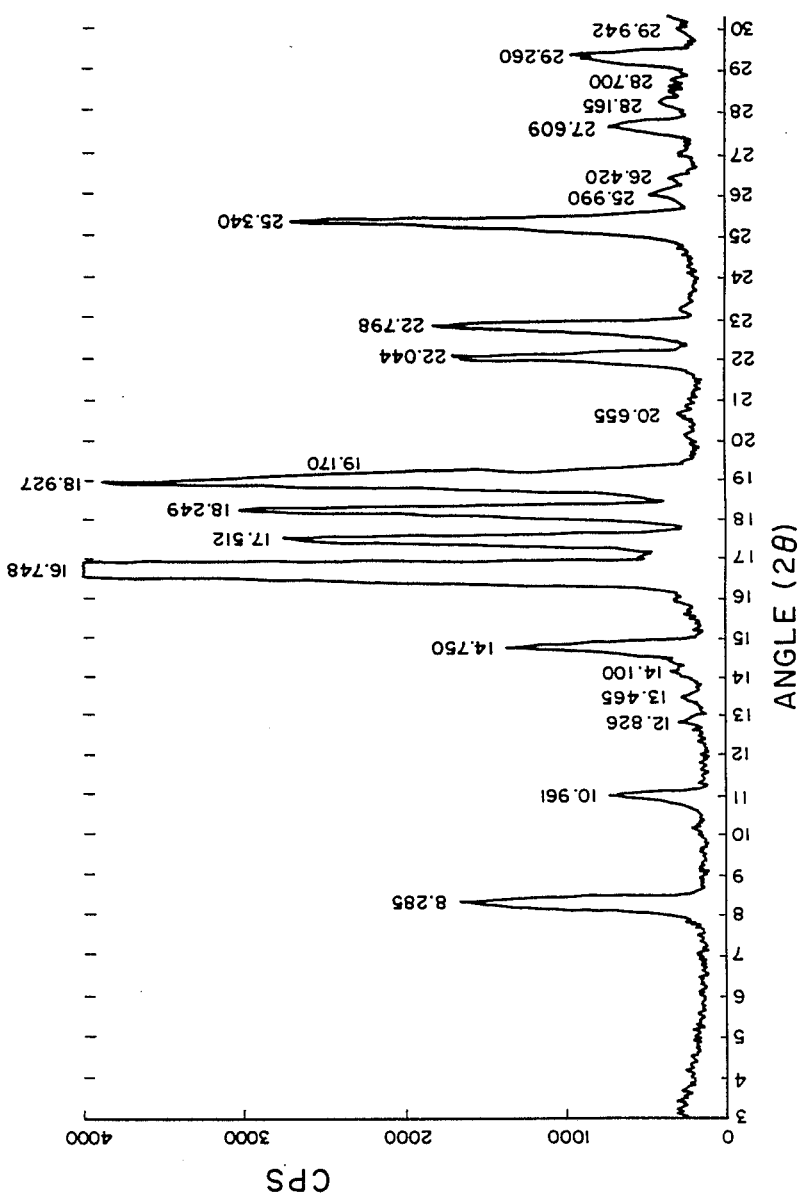
FIG. 1 to FIG. 3 show the X-ray powder diffraction pattern, the infrared absorption spectrum, and the curve of thermogravimetry (TG)-differential scanning calorimetry (DSC), respectively, of the Form II crystals.

Properties of Form II Crystals (i) Composition:
Monohydrate (ii) X-ray Powder Diffraction:
The diffraction pattern of Form II crystals recorded by monochromated Cu(K$\alpha$) radiation is shown in FIG. 1 in the values of diffraction angle 2$_{74}$ and the intensity I. The relation between interplannar spacing (d) and relative intensity (I/Io) in the characteristic peaks is shown in Table 1.

TABLE 1

| (Characteristic peaks of Form II) | |
|---|---|
| d (Å) | I/Io |
| 10.7 | 11.0 |
| 8.1 | 4.8 |
| 6.0 | 9.2 |
| 5.3 | 100.0 |
| 5.1 | 18.2 |
| 4.9 | 19.9 |
| 4.7 | 25.7 |
| 4.0 | 11.0 |
| 3.9 | 11.8 |
| 3.5 | 17.8 |
| 3.2 | 4.8 |
| 3.0 | 2.7 |

Figure 2:
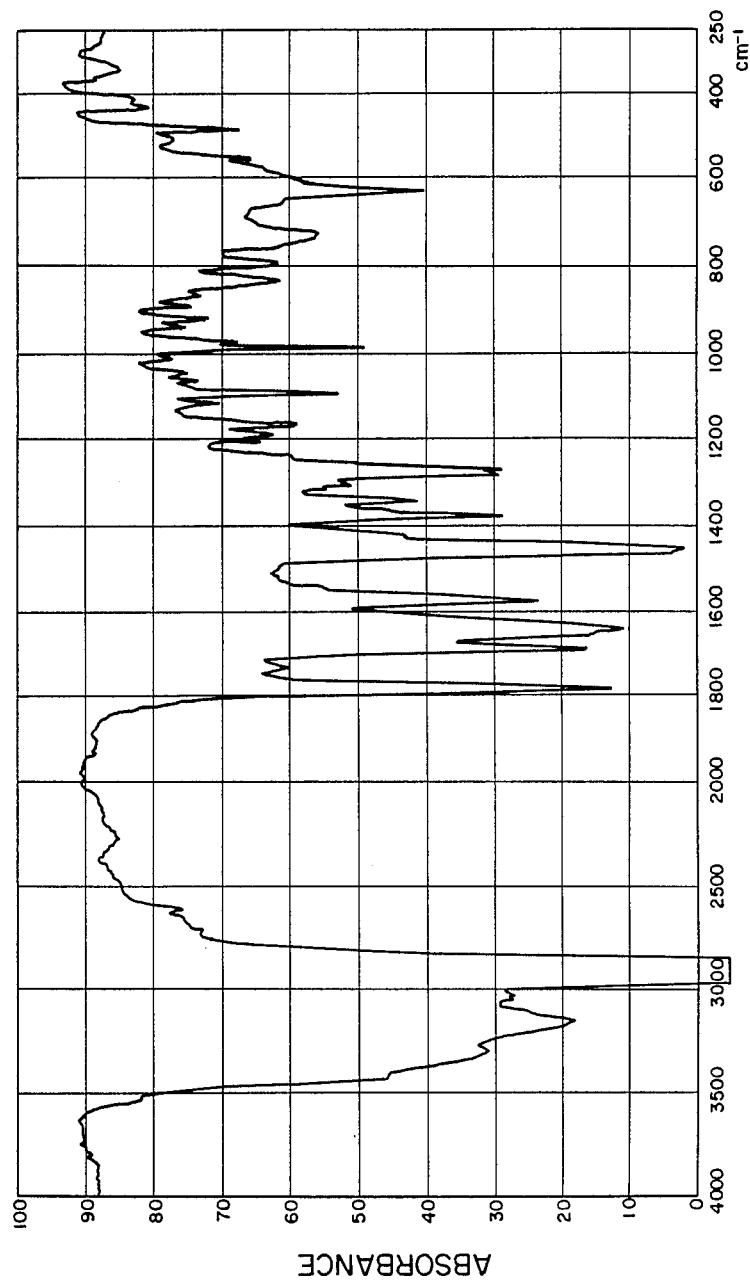

(iii) Infrared Absorption Spectrum:
The infrared absorption spectrum of the Form II crystals in Nujol mull is shown in FIG. 2. The carbonyl stretching vibration of the $\beta$-lactam ring, which is the characteristic absorption of the Form II crystals is 1780–1785 cm$^{-1}$.

Figure 3:
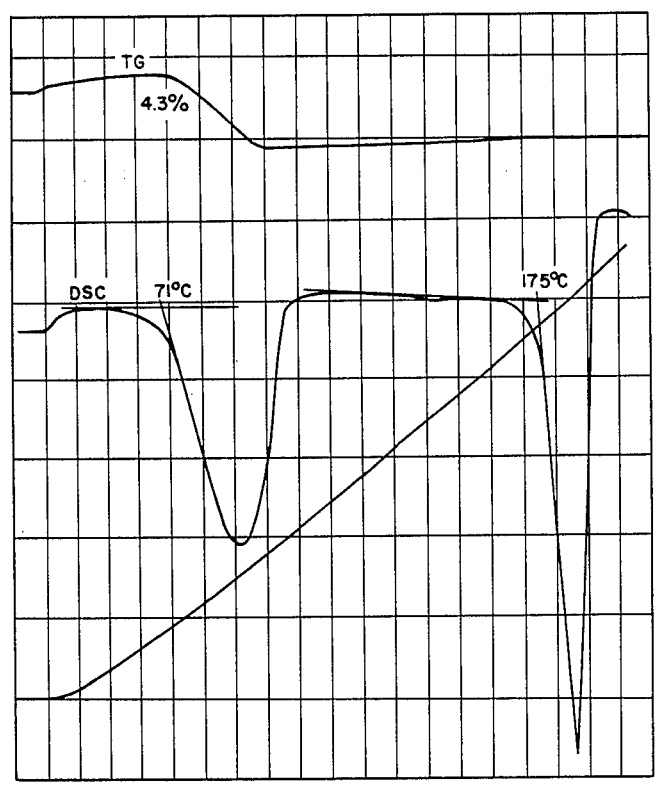

(iv) DSC and TG:
The TG-DSC curve of Form II crystals was recorded in ±2 mcal/sec of DSC full scale and 5 mg of TG full scale by heating to 200° C. in 5° C./min of the rate. The thermogram shown in FIG. 3 represents clearly an endothermic peak near 175° C. corresponded to the melting point, and weight loss in the TG curve.

Figure 4:
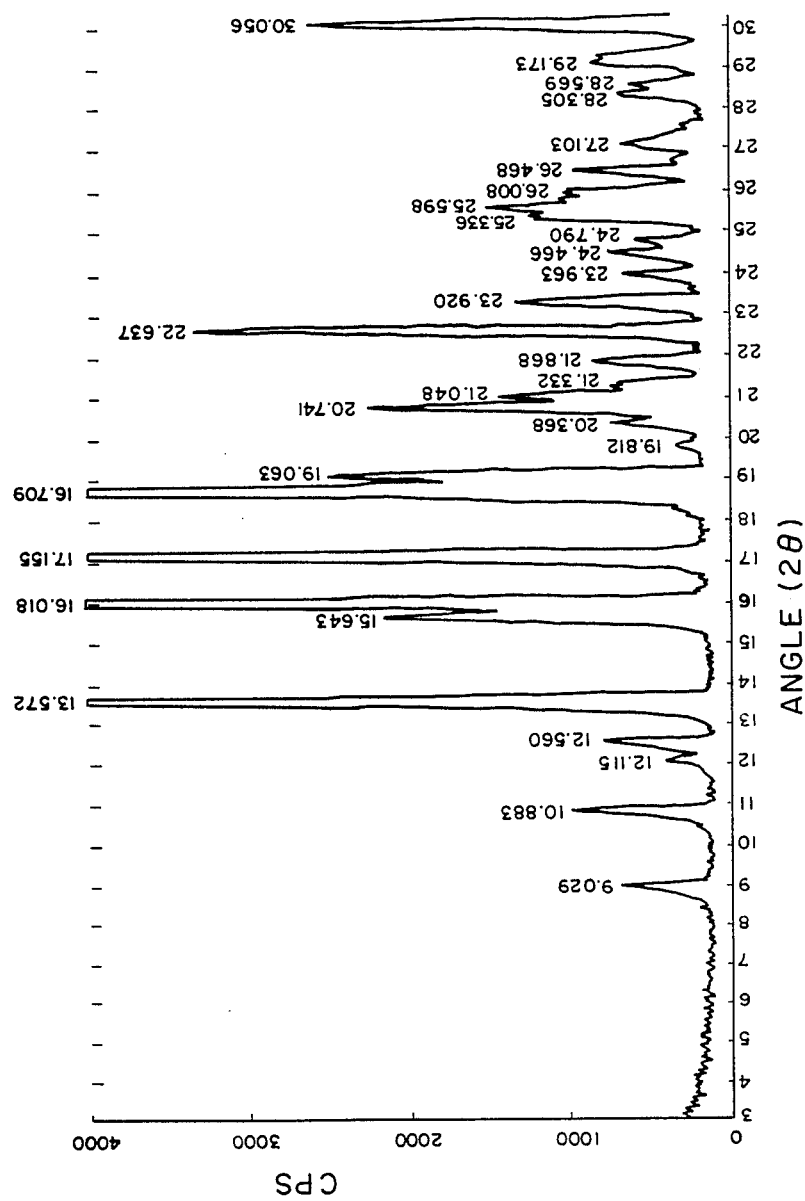
FIG. 4 to FIG. 6 show the X-ray powder diffraction pattern, the infrared absorption spectrum, and the TG-DSC curve, respectively, of the Form III crystals of this invention.

Properties of Form III Crystals (i) Conposition:
Dihydrate (ii) X-ray Powder Diffraction:
The diffraction pattern is shown in FIG. 4.
The characteristic peaks of the FOrm III crystals are shown in Table 2 by the relation between interplannar spacing (d) and the relative intensity (I/Io).

TABLE 2

| (Characteristic peaks of Form III) | |
|---|---|
| d (Å) | I/Io |
| 9.8 | 9.1 |
| 8.1 | 11.5 |
| 7.0 | 10.0 |
| 6.5 | 62.2 |
| 5.5 | 76.2 |
| 5.2 | 76.1 |
| 4.7 | 100.0 |
| 4.3 | 31.3 |
| 4.1 | 10.3 |
| 3.9 | 39.4 |
| 3.8 | 15.4 |
| 3.5 | 19.8 |
| 3.4 | 12.1 |
| 3.0 | 31.2 |

Figure 5:
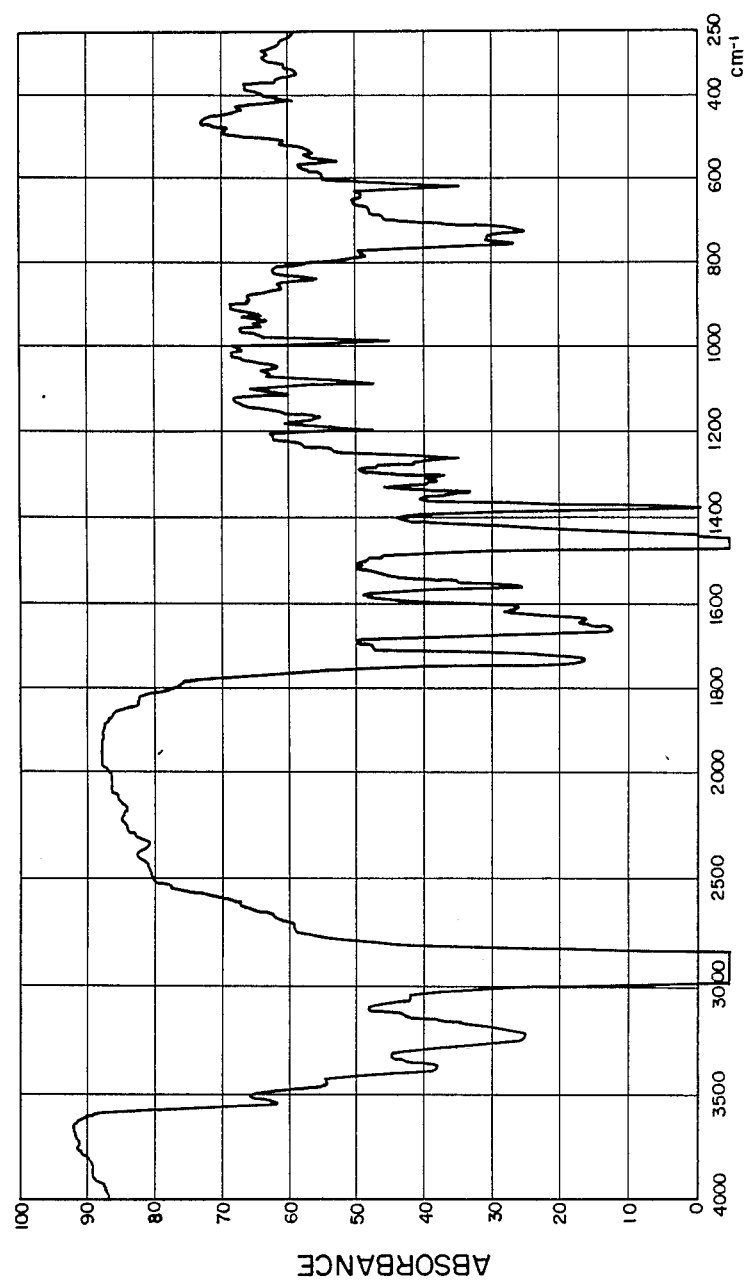

(iii) Infrared Absorption Spectrum:

The infrared absorption spectrum obtained by measuring under similar conditions as above is shown in FIG. 5.

The carbonyl stretching vibration of the β-lactam ring of the Form III crystals is 1730–1735 cm$^{-1}$.

Figure 6:
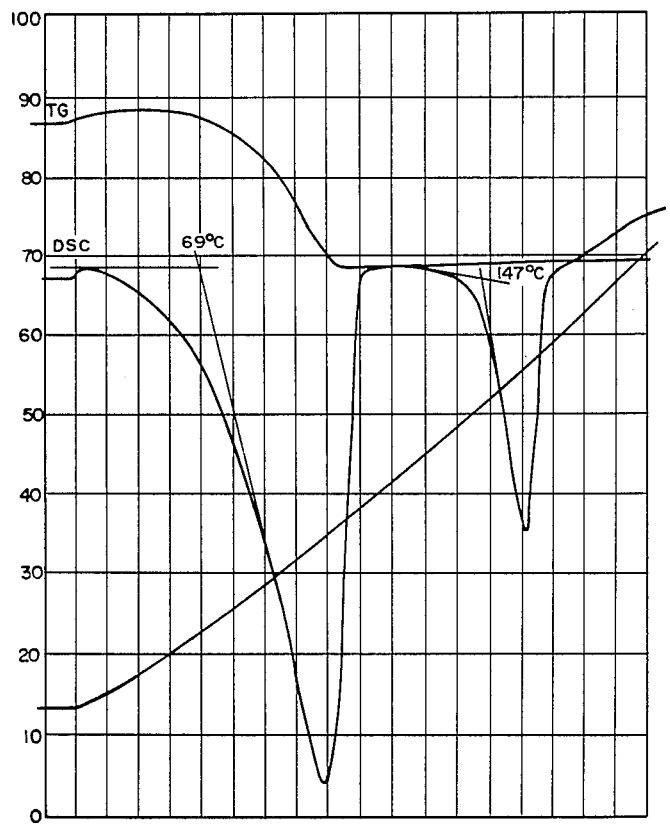

(iv) DSC and TG:

The curve of DSC-TG shown in FIG. 6 represents an endothermic peak near 147° C. corresponded to the melting point with weight loss in the TG curve.

Figure 7:
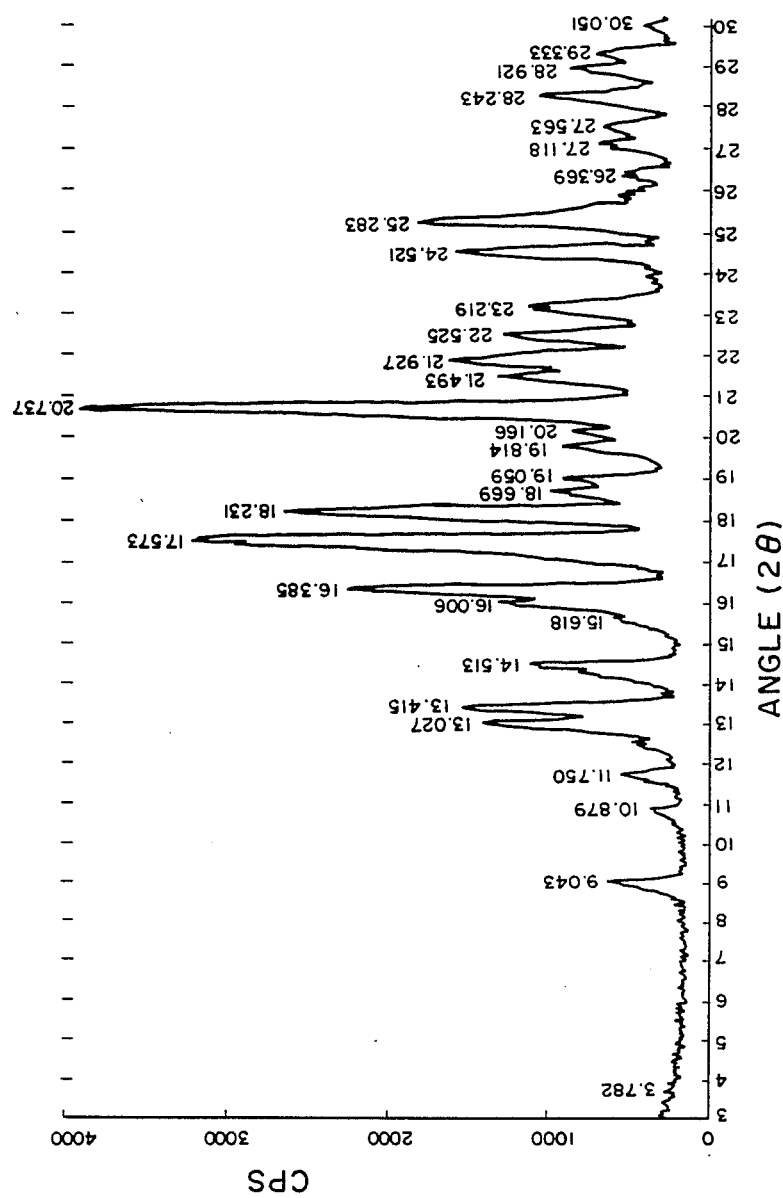
FIG. 7 and FIG. 8 show the X-ray powder diffraction pattern and the infrared absorption spectrum, respectively, of the Form IV crystals.

Properties of Form IV Crystals (i) Composition:
Anhydride (ii) X-ray Powder Diffraction:

The diffraction pattern obtained by measuring as the case of the Form II crystals is shown in FIG. 7.

The characteristic peaks of the Form IV crystals are shown in Table 3 by the relation between the interplannar spacing (d) and the relative intensity (I/Io).

TABLE 3

| (Characteristic peaks of Form IV) | |
| --- | --- |
| d (Å) | I/Io |
| 9.8 | 16.1 |
| 8.1 | 8.3 |
| 7.5 | 13.0 |
| 6.8 | 35.4 |
| 6.6 | 39.7 |
| 6.1 | 28.3 |
| 5.4 | 57.2 |
| 5.0 | 83.0 |
| 4.9 | 67.4 |
| 4.5 | 23.7 |
| 4.3 | 100.0 |
| 4.0 | 40.0 |
| 3.6 | 39.9 |
| 3.5 | 46.2 |
| 3.2 | 27.2 |

Figure 8:
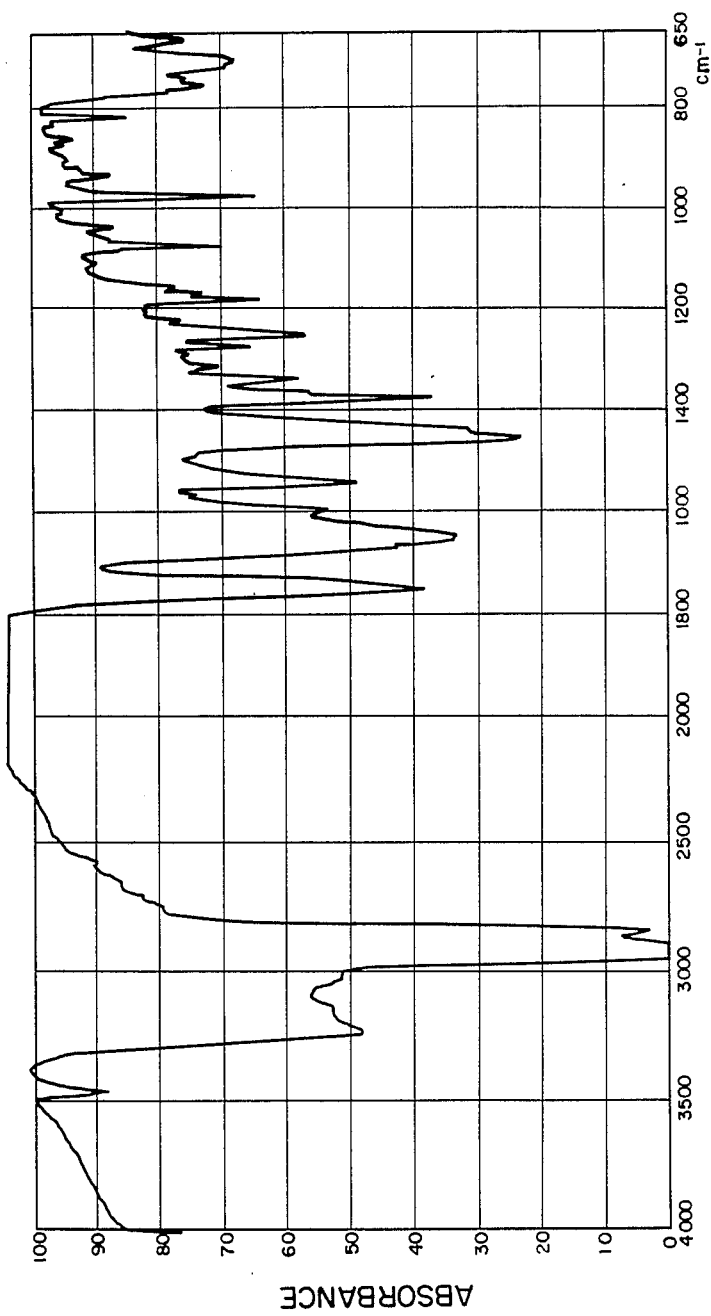

(iii) Infrared Absorption Spectrum:

The spectrum obtained by measuring under the same conditions as the case of the Form II crystals is shown FIG. 8.

The carbonyl stretching vibration of the β-lactam ring of the Form IV crystals is 1750–1755 cm$^{-1}$.

(iv) DSC and TG:

The Form IV crystals show an endothermic peak near 147° C. which is corresponding to the melting point.

Figure 9:
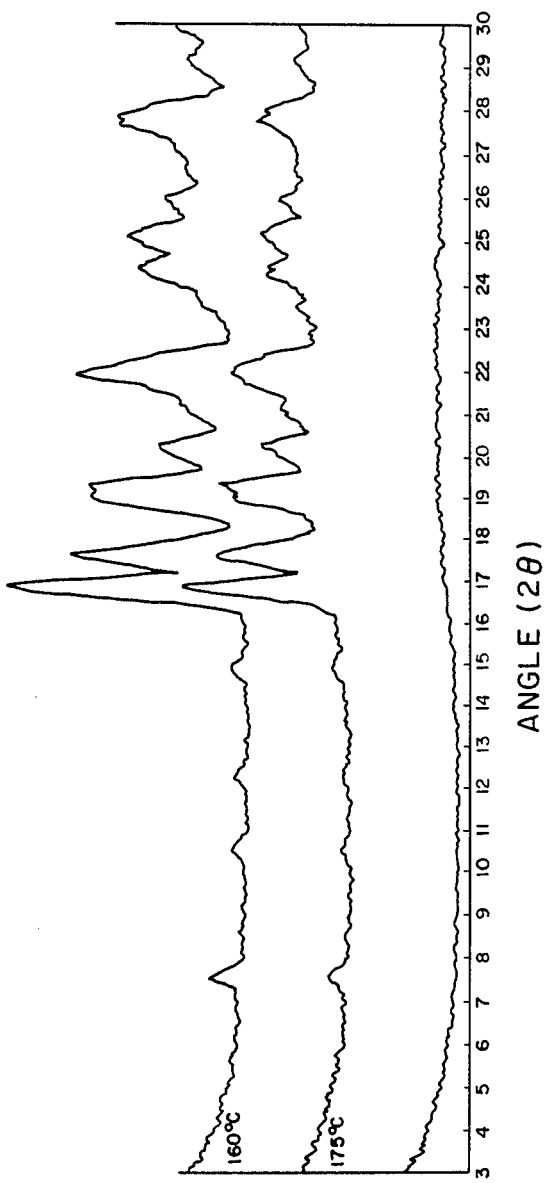
FIG. 9 shows the X-ray powder diffraction pattern of the form V crystals.

Properties of Form V Crystals (i) Composition:
Anhydride (ii) X-ray Powder Diffraction:

The diffraction patterns recorded at 160° C. and 175° C. by monochromated Cu(Kα) radiation are shown in FIG. 9 in the relation between the diffraction angle 2θ and the intensity.

(iii) Infrared Absorption Spectrum:

Because Form V crystals are very hygroscopic, the spectrum shows a mixture of Form V and Form II which was transformed from Form V by moisture during the measurement. The carbonyl stretching vibration of the β-lactam ring of Form V are 1755–1760 cm$^{-1}$, which can be easily distinguished from the absorption of Form II.

(iv) DSC and TG:

The curve shows an endothermic peak near 174° C. corresponded to the melting point.

These crystals of Compound A thus obtained are novel crystals each having different water content from that of the above-described known crystals of Compound A. In comparison of the stability among Forms I to V, Forms I, II, IV, and V are very hygroscopic and Form III is stable under conditions of ambient temperature and humidity without any change of the crystal form due to water adsorption or dehydration. Accordingly, Form III crystals are advantageous to storage, manipulation, formulation of Compound A and so on.

Preparations of Form III crystals

Process A: Compound A was recrystallized from methanol followed by drying at 60° C. under reduced pressure, and the resulting crystals (referred to as Form I crystals hereafter) were allowed to stand in 100% of relative humidity (RH), or Form II crystals were allowed to stand in 100% of RH.

Process B: The crystals of Compound A were suspended in water (2 to 6 times, preferably about 3 times) followed by stirring for about 1.5 to 3 hrs under ice-cooling, and the resulting crystals were collected by filtration followed by drying over a desicant agent such as silica gel.

Process C: The crystals of Compound A were dissolved in water (3 to 6 times, preferably 4 to 5 times) under heating, and the solution was ice-cooled. The recrystallized crystals were collected by filtration followed by drying overnight over a desicant agent such as silica gel.

Form II crystals can be obtained by allowing to the Form I crystals described above to stand in about 52% of RH. The state of 52% RH is obtained by placing a saturated aqueous solution of magnesium nitrate in a closed desiccator.

Form IV crystals are obtained by drying the Form III crystals over phosphorus pentaoxide at 40° to 65° C. under reduced pressure.

Preparations of Form V crystals

Process D: Form II crystals were dried over phosphorus pentaoxide at 40° to 65° C. under reduced pressure.

Process E: The crystals of Compound A were dissolved in about 10 times of ethanol under heating, and to the solution was added water in amount of 10% volume of ethanol under ice-cooling followed by keeping overnight in a refrigerator. The resulting crystals were collected by filtration followed by drying over phosphorus pentaoxide at 40° to 65° C. under reduced pressure.

In addition, the crystals of Compound A which are used for Process B, Process C and Process E described above may be any form.

Then, the production processes of the Forms II to V crystals of Compound A are more practically explained by the following reference examples and examples.

Reference Example 1 (Preparation of Form II):

Crude Compound A (1,415 g) was recrystallized from 26 liter of methanol. After drying at 60° C. under reduced pressure, 1,062 g of Form I crystals was obtained. The Form I crystals (4.08 g) placed on a dish (8.5 cm in diameter, 2 cm in depth) were allowed to stand in a closed desiccator containing saturated aqueous solution of magnesium nitrate for 24 hrs at room temperature. Form II crystals were quantitatively obtained.

The water content of the Form II crystals measured by Karl Fischer's method was 5.67%.

Elemental Analysis for $C_{15}H_{20}N_6O_4 \cdot H_2O$:

| | C (%) | H (%) | N (%) |
|---|---|---|---|
| Calculated: | 49.17 | 6.05 | 22.94 |
| Found: | 49.15 | 5.92 | 22.93 |

Figure 10:
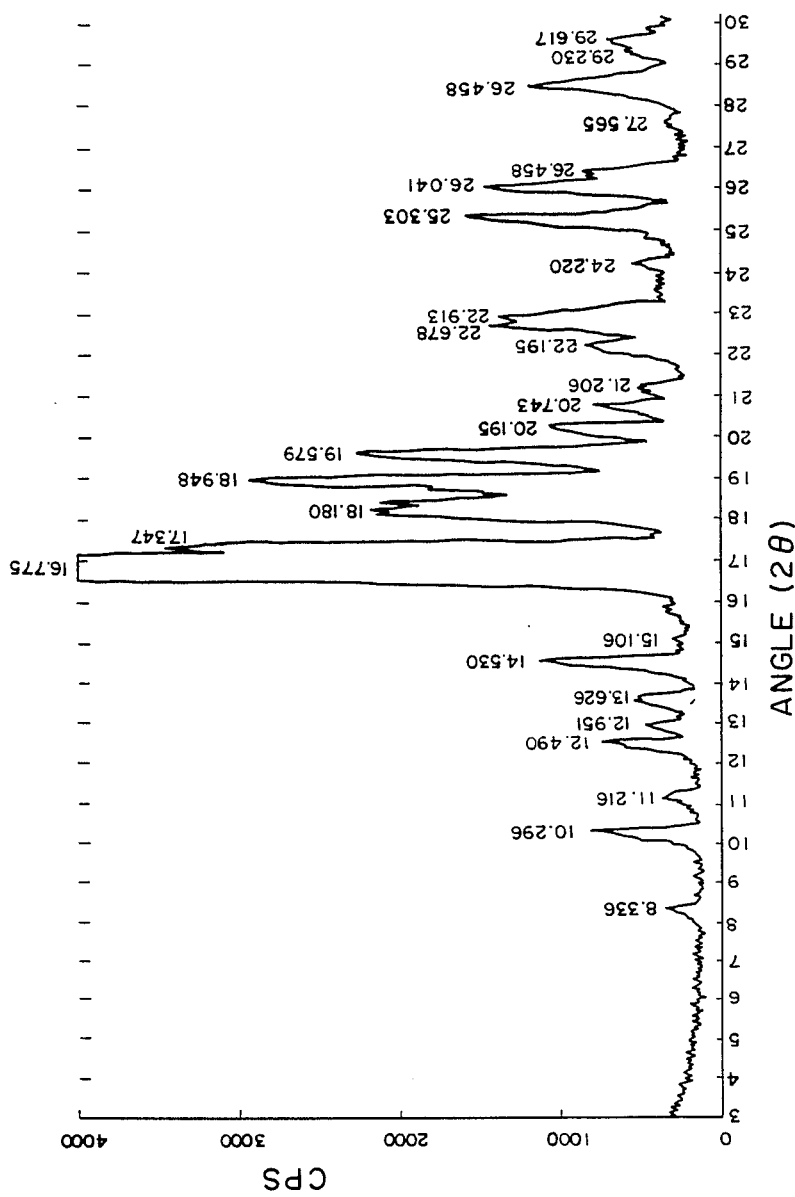
FIG. 10 to FIG. 12 show the X-ray powder diffraction pattern, the infrared absorption spectrum, and the TG-DSC curve, respectively, of Form I crystals of Compound A.
Figure 11:
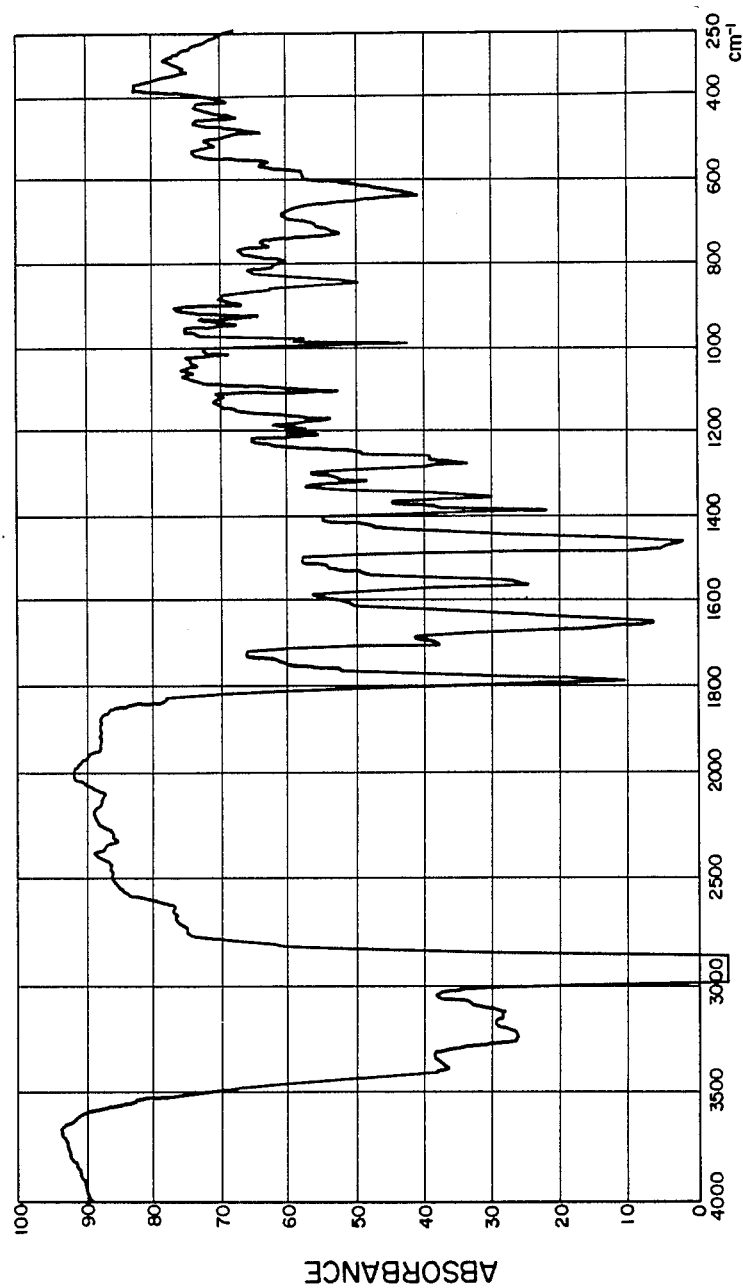
Figure 12:
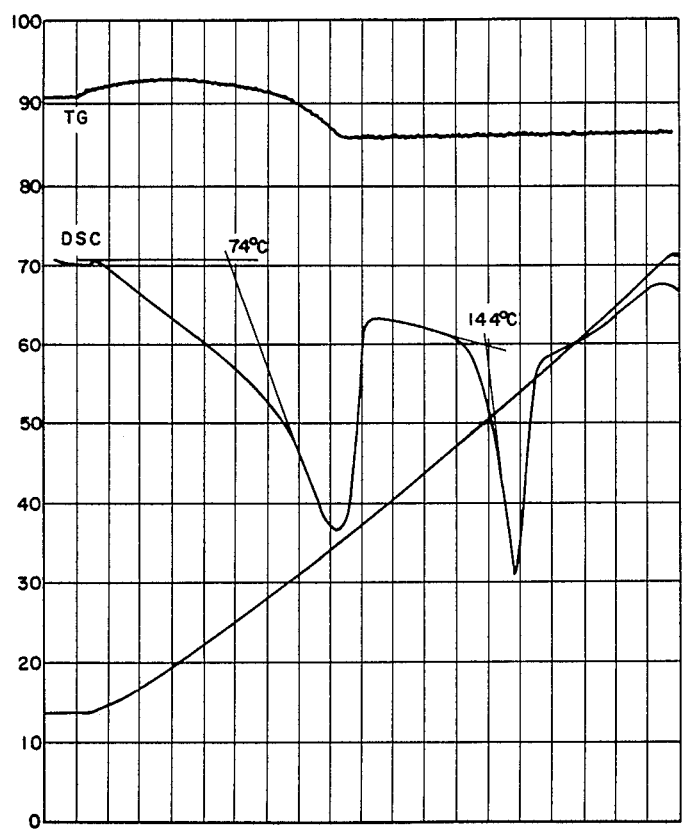

In addition, the X-ray powder diffraction pattern, the infrared absorption spectrum, and the DSC-TG curve of the Form I crystals as in the Form II crystals are shown in FIG. 10 to FIG. 12, respectively.

Example 1 (Preparation of Form III):

By allowing 4.08 g of the Form I crystals obtained in Reference Example 1 to stand in a closed desiccator containing water for 24 hours at room temperature, Form III crystals were obtained at a quantitative yield. By following the same procedure as above using the Form II crystals as a raw material, Form III crystals were also obtained.

The water content of the Form III crystals measured by Karl Fischer's method was 9.54%.

Elemental Analysis for $C_{15}H_{20}N_6O_4 \cdot 2H_2O$:

| | C (%) | H (%) | N (%) |
|---|---|---|---|
| Calculated: | 46.87 | 6.29 | 21.86 |
| Found: | 46.77 | 6.28 | 21.73 |

Example 2 (Preparation of Form III):

A mixture of 500 mg of Form I crystals of Compound A and 1.5 ml of cold water was stirred well for 2 hours under ice-cooling. Insoluble crystals were collected by filtration and dried overnight over silica gel to provide 422 mg of Form III crystals. The physicochemical properties of the crysals were same as those of the Form III crystals obtained in Example 1 described above.

Example 3 (Preparation of Form III)

In 30 ml of water was dissolved 7.0 g of Form I crystals of Compound A under heating and the solution obtained was ice-cooled. Crystals precipitated were collected by filtration and dried overnight over silica gel to provide 5.1 g of Form III crystals. The physicochemical properties of the crystals were same as those of the Form III crystals obtained in Example 1.

Reference Example 2 (Preparation of form IV)

By drying 3.0 g of the Form III crystals obtained in Example 1 at 60° to 65° C. under reduced pressure over phosphorus pentaoxide, 2.43 g of Form IV crystals was obtained.

Elemental Analysis for $C_{15}H_{20}N_6O_4$:

| | C (%) | H (%) | N (%) |
|---|---|---|---|
| Calculated: | 51.72 | 5.79 | 24.12 |
| Found: | 51.81 | 5.80 | 24.38 |

Reference Example 3 (Preparation of Form V)

By drying 355 mg of the Form II crystals obtained in Reference Example 1 at 60° to 65° C. under reduced pressure over phosphorus pentaoxide, Form V crystals were obtained. The elemental analysis thereof was immediately performed.

Elemental Analysis for $C_{15}H_{20}N_6O_4$:

| | C (%) | H (%) | N (%) |
|---|---|---|---|
| Calculated: | 51.72 | 5.79 | 24.12 |
| Found: | 51.31 | 5.58 | 24.18 |

Reference Example 4 (Preparation of Form V)

In 2.5 ml of ethanol was dissolved 250 mg of the Form I crystals of Compound A under heating and then 0.25 ml of water was added to the solution. The solution was ice-cooled and crystals precipitated were collected by filtration followed by drying at 60° to 65° C. over phosphorus pentaoxide to provide 195 mg of Form V crystals.

Comparison of the properties among Forms I to V of Compound A under various conditions is shown in Table 4 below. It is clear that the Form III crystals are most stable.

TABLE 4

| Crystals | Employed conditions at room temp. | Results |
|---|---|---|
| Form I | 100% of RH for one day | Form III |
| | 52% of RH for one day | Form II |
| | 33% of RH for 7 days | a mixture of Form I and Form II |
| | standing under ambient conditions for 4 days | a mixture of Form I and Form II |
| Form II | 100% of RH for one day | Form III |
| | 52% of RH for 12–18 days | a mixture of Form II and Form III |
| Form III | 100% of RH for 26 days | Form III |
| | standing under ambient conditions for 7 days | Form III |
| Form IV | 100% RH for 3–5 days | a mixture containing Form III |
| | 100% RH for 7–13 days | Form III |
| Form V | standing under ambient conditions for 3–10 min. | a mixture of Form II and Form V |

RH: relative humidity

What is claimed is:

1. Crystalline form of $N^\alpha$-[[(S)-4-oxo-2-azetidinyl]-carbonyl]-L-histidyl-L-prolinamide dihydrate having an X-ray powder diffraction pattern wherein the characteristic peaks of said crystals are shown below by the relation between interplannar spacing (d) and the relative intensity (I/Io):

| d (Å) | I/Io |
|---|---|
| 9.8 | 9.1 |
| 8.1 | 11.5 |
| 7.0 | 10.0 |
| 6.5 | 62.2 |
| 5.5 | 76.2 |
| 5.2 | 76.1 |
| 4.7 | 100.0 |
| 4.3 | 31.3 |
| 4.1 | 10.3 |
| 3.9 | 39.4 |
| 3.8 | 15.4 |
| 3.5 | 19.8 |
| 3.4 | 12.1 |
| 3.0 | 31.2. |

* * * * *